[54] 1,3-DISUBSTITUTED 3-AROYLPROPANES AND PROCESS FOR THE PREPARATION THEREOF

[75] Inventors: Elso Manghisi; Giuseppe Cascio, both of Monza, Italy

[73] Assignee: Istituto Luso Farmaco d'Italia S.r.l., Italy

[22] Filed: Apr. 18, 1973

[21] Appl. No.: 352,346

[30] Foreign Application Priority Data
Apr. 22, 1972 Italy .................................. 23444/72
Mar. 20, 1973 Italy .................................. 21881/73

[52] U.S. Cl. ...................... 260/268 PH; 260/246 B; 260/247.2 A; 260/247.2 B; 260/247.5 R; 260/247.5 F; 260/247.5 G; 260/268 R; 260/293.64; 260/293.71; 260/293.76; 260/293.78; 260/293.8; 260/326.43; 260/326.5 J; 260/477; 260/465 E; 260/561 R; 260/490; 260/570.6; 260/570.7; 260/570.9; 260/268 H; 260/570.8 R; 424/250
[51] Int. Cl.² .............. C07D 295/10; C07D 295/12
[58] Field of Search ................... 260/268 PH, 268 H

[56] References Cited
UNITED STATES PATENTS
2,997,472  8/1961  Janssen ......................... 260/268 PH
3,210,368  10/1965  Huebner ......................... 260/306.8
3,732,229  5/1973  Bysouth et al. ............... 260/268 PH

FOREIGN PATENTS OR APPLICATIONS
1,185,615  1/1965  Germany

Primary Examiner—R. Gallagher
Assistant Examiner—Jose Tovar
Attorney, Agent, or Firm—Hill, Gross, Simpson, Van Santen, Steadman, Chiara & Simpson

[57] ABSTRACT

1,3-Disubstituted-3-aroylpropanes of the formula:

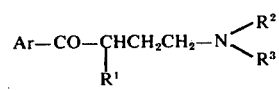

and their salts, in which Ar represents an aryl residue unsubstituted or substituted by halogen, polyhalogeno alkyl or lower alkoxy; $R^1$ represents an hydroxy, acyloxy, carbamoyloxy, alkylcarbamoyloxy, dialkylcarbamoyloxy, aroyloxy, alkoxy, aryloxy, or cyano group or an amino group of the formula:

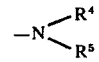

which can be the residue of a secondary amine, a tertiary amine, or of a heterocyclic amine; and

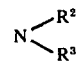

represents the residue of a secondary amine, a tertiary amine, or of a heterocyclic amine, have interesting properties as analgesic agents, anti-arrhythmic agents, and central nervous depressants.

11 Claims, No Drawings

1,3-DISUBSTITUTED 3-AROYLPROPANES AND PROCESS FOR THE PREPARATION THEREOF

The present invention provides, as new compounds, the 1,3-disubstituted-3-aroylpropanes of the formula

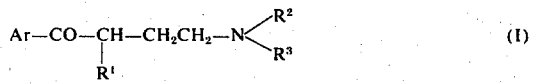

in which Ar represents an aryl residue, unsubstituted or substituted by one or more halogen atoms, polyhalogeno-alkyl groups, or lower alkoxy groups; $R^1$ represents either a hydroxy, acyloxy, carbamoyloxy, alkyl-carbamoyloxy, dialkyl-carbamoyloxy, aroyloxy, alkoxy, aryloxy, or cyano group, or an amino group having the formula

which can be the residue of a secondary amine (methylamino, ethylamino, propylamino, isopropylamino, benzylamino, phenylethylamino etc.), or of a tertiary amine (dimethylamino, diethylamino, diethanolamino, dibenzylamino, etc.), or of a heterocyclic amine (morpholino, pyrrolidino, piperidino, 4,4-disubstituted-piperidino, piperazino, N-methylpiperazino, N-hydroxyethylpiperazino, N-phenylpiperazino, N-o-methoxyphenylpiperazino etc.); and

represents the residue of a secondary amine (methylamino, ethylamino, propylamino, isopropylamino, benzylamino, phenylethylamino etc.), or of a tertiary amine (dimethylamino, diethylamino, diethanolamino, dibenzylamino etc.), or of a hetero-cyclic amine (morpholino, pyrrolidino, piperidino, 4-substituted piperidino, 4,4-disubstituted-piperidino, spiro-piperidino, piperazino, N-methylpiperazino, N-hydroxyethyl-piperazino, N-phenylpiperazino, N-o-methoxyphenyl-piperazino, N-2-pyridyl-piperazino etc.). Especially valuable are those compounds in which Ar is phenyl, p-chlorophenyl, p-fluorophenyl, or p-methoxyphenyl, $R^1$ is hydroxy, alkanoyloxy of up to 4 carbon atoms, carbamoyloxy, alkylcarbamoyloxy of up to 5 carbon atoms, dialkylcarbamoyloxy of up to 4 carbon atoms in each alkyl, benzoyloxy, 3,4,5-trimethoxybenzoyloxy, phenoxy, α-naphthoxy, cyano, or morpholino, and either $R^2$ and $R^3$ are each alkyl of 1 to 4 carbon atoms, or

is pyrrolidino, piperidino, morpholino, 4-phenyl-piperazino, 4-hydroxy-4-p-chlorophenyl-piperidino, 4-o-methoxyphenyl-piperazino, 4-benzamido-piperidino, or 4-2'-pyridyl-piperazino, 4-(2-keto-1-benzimidazolinyl)piperidino, 8-(1-phenyl-1,3,8-triazaspiro[4,5]decan-4-one) in racemic and optically active forms, and their pharmaceutically acceptable acid addition salts.

According to a feature of the invention, the aforesaid compounds are made by reacting a compound having the formula:

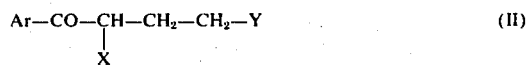

in which X and Y represent atoms of halogen, with an alcoholate of an alkali or alkaline earth metal (such as sodium methylate), to produce an intermediate product of, e.g. the general formula:

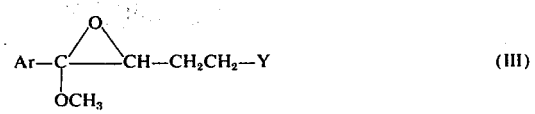

and reacting this intermediate with an amine of the formula

to produce a final product in which $R^1$ represents a hydroxy group:

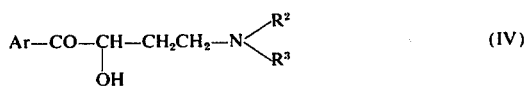

The reaction of the compounds of formula II with the alcoholate should take place in an anhydrous medium, e.g. by mixing the two reagents in an excess of alcohol and leaving the mixture to stand for 24 hours. If the metal alcoholate is replaced by a metal salt of a phenol or of an aliphatic or aromatic carboxylic acid, the intermediate product obtained has the formula:

where $R^1$ represents an aryloxy, acyloxy or aroyloxy residue, and Y is a halogen atom. This intermediate is then reacted with the amine of formula

and a compound of formula I in which $R^1$ is as first stated, is obtained.

The acyloxy- and aroyloxy derivatives can also be obtained by reaction of compounds of the formula IV with the corresponding aliphatic or aromatic acids or preferably a reactive derivative thereof (phosgene, acid chloride, anhydride, mixed anhydride, ester, isocyanate, etc.).

When a compound of formula II is heated with an excess of amine of formula

products are obtained of the formula:

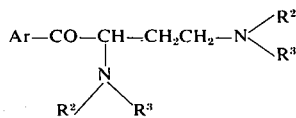

When, in the compounds of formula II, X represents an atom of bromine and Y an atom of chlorine, it is possible for the bromine atom to be selectively replaced by reaction with an amine of formula

at room temperature, thus producing an intermediate product having the formula

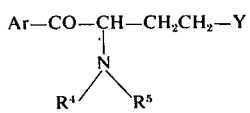

which can then be heated with an amine of formula

different from the amine of formula HNR⁴R⁵ thereby producing a compound of formula I, in which R¹ represents an amino residue different from that attached in the terminal position.

According to another feature of the invention, a compound of the formula

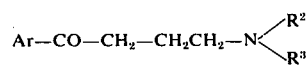

is brominated to produce a compound of the formula:

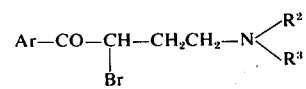

which, is then reacted with a metallic salt of an alcohol, phenol, acid or amine to produce a compound of formula I.

When R¹ represents a cyano group, the preparation method consists in making the sodium salt of a compound of the formula

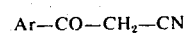

and heating it in an aqueous medium with a compound of formula

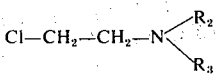

to produce directly the compound of formula I.

The compounds of formula I contain an asymmetric carbon atom in a position alpha to the carbonyl. The compounds can therefore be divided into their optical antipodes by standard methods, such as salification with an optically active acid and separation by fractional crystallisation of the two salts.

Salts of the compounds of formula I can be prepared with pharmaceutically acceptable inorganic acids, e.g. hydrochloric, hydrobromic, nitric, sulphuric, and phosphoric acids etc, as well as with organic carboxylic acids, such as acetic, propionic, glycolic, malonic, succinic, maleic, hydroxy maleic, fumaric, malic, tartaric, citric, glucuromic, benzoic, mandelic, salicylic, 4-aminosalicylic, 2-phenoxybenzoic, 2-acetoxybenzoic, pamoic, nicotinic and isonicotinic acids etc, or with organic sulphonic acids, such as methane sulphonic, ethanesulphonic, 2-hydroxyethanesulphonic, 1,2-ethane-disulphonic, p-toluenesulphonic and naphthalene-2-sulphonic acids etc. Mono or poly salts are formed depending on the number of salifiable groups present in the molecules.

The compounds of formula I and their pharmaceutically acceptable salts (in racemic and optically active forms) have considerable analgesic and anti-arrhythmic properties and are also depressants of the central nervous system. They can be given orally or by injection in the appropriate pharmaceutical preparations in a solid, liquid or suspension form (tablets, capsules, phials, lincti, etc.).

The Tables below summarize the pharmacological features of particular compounds of the present invention, designated as follows:

LR 320 : 1-p-fluorobenzoyl-1,3-dimorpholino-propane

LR 340 : 1-benzoyl-1-cyano-3-diethylamino-propane citrate

LR 343 : 1-p-fluorobenzoyl-1-hydroxy-3-piperidino propane maleate

LR 352 : 1-p-fluorobenzoyl-1-cyano-3-diethylamino-propane citrate

LR 363 : 1-p-fluorobenzoyl-1-hydroxy-3-N-(N'-phenyl) piperazino propane

LR 370 : 1-p-fluorobenzoyl-1-(3',4',5'-trimethoxybenzoyloxy)-3-N-piperidino propane maleate LR 401 : 1-p-fluorobenzoyl-1-phenoxy-3-N-(N'-phenyl)piperazino propane LR 402 : 1-p-fluorobenzoyl-1-phenoxy-3-piperidino-propane maleate LR 414 : 1-p-fluorobenzoyl-1-hydroxy-3-N-(4-hydroxy-4-p-chlorophenyl) piperidino-propane.

LR 415 : 1-p-fluorobenzoyl-1-acetoxy-3-N-(N'-phenyl) piperazino propane maleate

LR 442 : 1-p-fluorobenzoyl-1-(α-naphthoxy)-3-morpholinopropane

LR 452 : 1-p-fluorobenzoyl-1-morpholino-3-piperidinopropane dihydrochloride

LR 535 : 1-p-fluorobenzoyl-1-N-dimethyl carbamoyloxy-3-N-(N'-phenyl) piperazino propane dihydrochloride LR 541 : 1-p-fluorobenzoyl-1-N-tert-butyl-carbamoyloxy-3-N-(N'-phenyl) piperazino propane.

The decrease in the spontaneous motility has been assessed in mice according to J. Maj, H. Sowinska, L.

Baran, Z. Kapturkiewicz (Life Sciences, vol. 11, part I, 483–491, 1972), whereas the antogonism to apomorphine has been assessed in the rat (P. A. J. Janssen, C. J. E. Niemegeers, K. H. L. Schellekens - Arzneimittel-Forschung, 15, 104–117, 1965).

The analgesic action in mice (stretching caused by acetic acid) has been assessed according to the method of Arrigoni and E. Martelli (Boll. Chim. Farm. 107, 29, 1968), whereas the anti-arrhythmic action in rats has been assessed according to the method of M. R. Malinow, F. F. Battle and B. Malamud (Arch. Intern. Pharmacodynamie, 102, 226, 1955).

The results obtained were as follows:

| Substance | Acute Toxicity Mouse mg/Kg/ip *$LD_{50}$ | Reduction Spontaneous motility Mouse mg/Kg/os | Apomorphine Antagonism Rat mg/Kg/os |
|---|---|---|---|
| LR 320 | 540 | 100 = 23% | — |
| LR 340 | 60 | — | 5.5 = 50% |
| LR 343 | 125 | 25 = 24% | 11.5 = 50% |
| LR 352 | 250 | — | 50 = 40% |
| LR 363 | >1000 | 35 = 50% | 200 = 20% |
| LR 370 | 400 | 40 = 40% | 80 = 20% |
| LR 401 | >1000 | 200 = 50% | — |
| LR 402 | 75 | 7.5 = 33% | — |
| LR 414 | 55 | 9.8 = 50% | 10 = 20% |
| LR 415 | 575 | 56 = 50% | — |
| LR 442 | >1000 | 56 = 50% | — |
| LR 535 | 150 | 30 = 50% | 40 = 30% |
| LR 541 | >1000 | 200 = 50% | — |

*LD = Lethal dose

| Substance | Acute Toxicity Mouse mg/Kg/ip *$LD_{50}$ | Analgesic Action (stretching acetic acid) Mouse mg/Kg/os | Antiarrhythmic Action-$CaCl_2$ Rat mg/Kg/iv |
|---|---|---|---|
| LR 320 | 540 | 80 = 50% | — |
| LR 340 | 60 | 12 = 50% | — |
| LR 343 | 125 | 25 = 22% | — |
| LR 352 | 250 | 22.7 = 50% | — |
| LR 452 | 100 | — | 3.9 = 50% |
| LR 535 | 150 | — | 10 = 20% |

*LD = lethal dose

The following examples illustrate the invention. The melting and boiling points are not corrected.

The identity of the substances and the purity thereof have been checked by elementary analyses of the carbon, hydrogen and nitrogen (and halogens where present), infra-red spectra, N.M.R. and U.V. spectra.

EXAMPLE 1

1-p-Fluorobenzoyl-1,3-dimorpholino-propane.

A solution of 10 g. of 1-p-fluorobenzoyl-1-bromo-3-chloro-propane, 12.5 g. of morpholine and a catalytic quantity of potassium iodide in 100 cc. xylene is made to reflux for 12 hours and then cooled. The resulting solid is filtered and the filtrate extracted with dilute HCl. The separated aqueous phase is filtered hot using animal charcoal, cooled, made alkaline with dilute soda solution, and extracted with diethyl ether. The organic phases are combined, washed with water, dried and evaporated, m.p. : 82°C (from hexane).

EXAMPLE 2

1-p-Fluorobenzoyl-1-morpholino-3-piperidino-propane dihydrochloride.

A solution of 12 g. of 1-p-fluorobenzoyl-1-morpholino-3-chloropropane, 7.15 g. of piperidine and a catalytic quantity of potassium iodide in 150 cc. toluene is refluxed for 20 hours and cooled. The resulting solid is filtered and the organic phase is washed with water until it is neutral. It is then dried and evaporated. The residual oil is chromatographed on alumina eluting with hexane. The dihydrochloride is precipitated by drying and adding alcoholic HCl: m.p. 205°-10°C (alcohol).

The starting material is prepared as follows.

15 g. of 1-p-fluorobenzoyl-1-bromo-3-chloropropane, 9.4 g. of morpholine and a catalytic quantity of potassium iodide in 100 cc anhydrous benzene are stirred at room temperature for 36 hrs. The resulting solid is filtered and the filtrate extracted with dilute HCl. The aqueous phase is separated, made alkaline, under cold conditions, with dilute soda solution, and extracted with diethyl ether. The extract is dried and evaporated to give 1-p-fluorobenzoyl-1-morpholino-3-chloropropane.

The latter is purified by transforming it into the corresponding maleate (m.p. 134°C from alcohol) and subsequent reconversion of the salt into the base.

EXAMPLE 3

1-p-Chlorobenzoyl-1-morpholino-3-pyrrolidinopropane dihydrochloride.

5 g. of 1-p-chlorobenzoyl-1-bromo-3-pyrrolidinopropane hydrobromide (obtained by bromination of 1-p-chlorobenzoyl-3-pyrrolidinopropane, as described in the U.S. Pat. No. 3,189,600), 3.17 g. of morpholine and a catalytic quantity of potassium iodide in 100 cc benzene are refluxed for 12 hours and then cooled. The solid is filtered off and the filtrate is washed with water, dried and evaporated. The resiude is converted into the corresponding dihydrochloride, m.p. : 198°C (from alcohol).

EXAMPLE 4

1-p-Fluorobenzoyl-1-phenoxy-3-piperidinopropane maleate.

15 g. of 1-p-fluorobenzoyl-1-phenoxy-3-chloropropane, 8.7 g. of piperidine and a catalytic quantity of potassium iodide in 100 cc. toluene are refluxed for 20 hours. After cooling, the solid formed is filtered off and the filtrate is extracted with dilute HCl. The separated aqueous phase is made alkaline under cold conditions with a 20% solution of NaOH and then extracted several times with chloroform. The separated organic phase is dried over $Na_2SO_4$, filtered and evaporated to dryness under reduced pressure. The residue is an oil which is converted into the corresponding maleate: m.p. 140°C (from alcohol).

Analogously, can be prepared: 1-p-Fluorobenzoyl-1-phenoxy-3-N-(N'-phenyl)piperazinopropane, m.p. 115° C (from alcohol).

The 1-p-Fluorobenzoyl-1-phenoxy-3-chloropropane is prepared as follows: a solution of 30 g. of 1-p-fluorobenzoyl-1-bromo-3-chloropropane in 100 cc. anhydrous acetone is added slowly, during half an hour and with stirring, to a suspension of 10.1 g. of phenol, 1.08 g. sodium iodide and 25.2 g. K$_2$CO$_3$ in 350 cc. anhydrous acetone. When the addition is complete, the mixture is refluxed for 12 hours. The solid contained therein is filtered off and the filtrate is evaporated to dryness under reduced pressure. The residual oil is fractionated in a vacuum and the product is collected as a yellow oil. (b.p. 165°–70°C/0.6 Torr).

EXAMPLE 5

1-p-Fluorobenzoyl-1-(alpha-naphthoxy)-3-morpholinopropane 15 g. of 1-p-fluorobenzoyl-1-(alpha-naphthoxy)-3-chloropropane, 7.6 g. of morpholine and a catalytic quantity of potassium iodide in 150 cc xylene are refluxed for 15 hours. The product is cooled, the solid therein is filtered off, and the filtrate is extracted with dilute HCl. The separated aqueous phase is made alkaline under cold conditions with 20% NaOH solution and then extracted several times with benzene. The collected benzene extracts are washed in water until neutral, dried over Na$_2$SO$_4$, filtered and evaporated to dryness (m.p. 101°C from EtOH).

The 1-p-Fluorobenzoyl-1-(alpha-naphthoxy)-3-chloropropane is prepared as follows. A solution of 20 g. of 1-p-fluorobenzoyl-1-bromo-3-chloropropane in 60 cc. anhydrous acetone is added slowly over half an hour while stirring to a suspension of 10.4 g. of α-naphthol, 0.72 g. of sodium iodide and 16.8 g. of K$_2$CO$_3$ in 300 cc. anhydrous acetone. When the addition is complete, the mixture is refluxed for 10 hours and then cooled. The solid therein is filtered off and the solvent is removed from the filtrate at reduced pressure. The residue melts at 147°C (from benzene).

EXAMPLE 6

1-p-fluorobenzoyl-1-hydroxy-3-N-(N'-phenyl)-piperazinopropane 20 g. of 1-p-fluorophenyl-1-methoxy-4-chloro-1,2-epoxybutane, 39.5 g. of N-phenyl-piperazine and a catalytic quantity of potassium iodide in 250 cc toluene are refluxed for 20 hours and then cooled. The resulting solid is filtered off and the filtrate is extracted with dilute HCl. A solid precipitates during extraction in the aqueous phase and it is filtered off, washed on the filter with diethyl ether, dried in a vacuum, suspended in water and made alkaline with dilute NaOH. The suspension is extracted several times with chloroform. The combined organic extracts are washed with water, dried and evaporated. The residue melts at 134°C (from alcohol)

Analogously can be prepared:
1-p-Fluorobenzoyl-1-hydroxy-3-N-(4-hydroxy-4-p-chlorophenyl)piperidinopropane, m.p. = 156°C (from alcohol); 1-p-fluorobenzoyl-1-hydroxy-3-piperidinopropane maleate m.p. = 106°C (from alcohol); 1-p-fluorobenzoyl-1-hydroxy-3-N-(N'-o-methoxy-phenyl)-piperazino propane, m.p. 108°C (from alcohol); 1-benzoyl-1-hydroxy-3-N-(N'-phenyl)piperazinopropane, m.p. = 145°C (from alcohol); 1-p-chlorobenzoyl-1-hydroxy-3-N-(N'-phenyl)piperazinopropane, m.p. = 155°C (from alcohol); 1-p-methoxybenzoyl-1-hydroxy-3-N-(N'-phenyl)piperazinopropane, m.p. = 138°C (from alcohol); 1-p-fluorobenzoyl-1-hydroxy-3-(4-benzamido-piperidino)propane, m.p. = 152°C (from alcohol); 1-p-fluorobenzoyl-1-hydroxy-3-[4-(2-keto-1-benzimidazolinyl)piperidino]propane, m.p. = 167°C (from alcohol); 1-p-fluorobenzoyl-1-hydroxy-3-[8-(1-phenyl-1,3,8-triazaspiro[4,5]decan-4-one)]-propane, m.p. = 185°C (from alcohol). 1-p-fluorobenzoyl-1-hydroxy-3-N-(N'-2-pyridyl)-piperaziro-propane, m.p. = 104°C (from alcohol). The 1-p-fluorophenyl- 1-methoxy-4-chloro-1,2-epoxybutane is prepared as follows: 100 grams of 1-p-fluorobenzoyl-1-bromo-3-chloropropane (prepared from 1-p-fluorobenzoyl-3-chloropropane with bromine in acetic acid) dissolved in 250 cc absolute methanol are added to a solution of sodium methylate, obtained by dissolving 8.25 g. of sodium in 300 cc. absolute methanol. The addition is carried out all at once, at room temperature. The product is left for 24 hours. The solvent is removed under reduced pressure. The residue is taken up again with diethyl ether and filtered. The filtrate is evaporated to dryness in a vacuum, to give a light yellow oil used for the subsequent reactions without further purification.

Analogously can be obtained:
1-Benzoyl-1-methoxy-4-chloro-1,2-epoxy butane; 1-p-chlorobenzoyl-1-methoxy-4-chloro-1,2-epoxy butane and 1-p-methoxybenzoyl-1-methoxy-4-chloro-1,2-epoxy butane.

EXAMPLE 7

1-p-Fluorobenzoyl-1-(3',4',5'-trimethoxy-benzoyloxy)-3-N-piperidinopropane maleate 6.5 g. of 1-p-fluorobenzoyl-1-hydroxy-3-N-piperidinopropane and 8 g. of 3,4,5-trimethoxybenzoylchloride in 11.7 g. anhydrous pyridine are refluxed for 4 hours. The product is cooled and the pyridine is removed in a vacuum. The residue is dissolved in benzene and washed with a saturated solution of sodium bicarbonate. The separated organic phase is dried and evaporated in a vacuum to give an oil which is transformed into the corresponding maleate: m.p. 166°C (from alcohol).

EXAMPLE 8

1-p-Fluorobenzoyl-1-acetyloxy-3-N-(N'-phenyl)-piperazinopropane maleate.

3.6 g. of anhydrous potassium acetate is added to a solution of 10 g. of 1-p-fluorobenzoyl-1-bromo-3-chloropropane in 30 cc CH$_3$—COOH and heated for 8 hours at 120°C. It is then cooled and the solid therein is filtered off. The filtrate is evaporated under reduced pressure. The residue is dissolved in 100 cc toluene to which 11.7 g of N-phenylpiperazine and a catalytic quantity of potassium iodide are added, and refluxed for 20 hours. The reaction mixture is cooled, the solid therein is filtered off and the filtrate is extracted with dilute HCl. The separated aqueous phase is filtered using charcoal, made alkaline with 20% NaOH solution under cold conditions and then extracted with diethyl ether. The separated organic phase is dried over Na$_2$SO$_4$ and evaporated to give an oil which is transformed into the corresponding maleate. m.p.: 159°C (from alcohol).

EXAMPLE 9

1-p-Fluorobenzoyl-1-cyano-3-diethylaminopropane citrate.

To a suspension of 5 g. of α-cyano-p-fluoroacetophenone in 100 cc. water is added, with vigorous stirring, 1.22 g. of NaOH dissolved in 5 cc water. When the solution is homogeneous, it is heated at 40°C and 4.55 g. of diethylaminoethylchloride are added drop by drop. Once the addition is complete, the product is heated to 70°C with continued stirring for 12 hours. It is then cooled and the reaction mixture is extracted first with ether and then with benzene. The combined ether and benzene extracts are dried over $Na_2SO_4$, filtered and evaporated under reduced pressure. The residual oil is transformed into the corresponding citrate: m.p. 128°C (from alcohol-ether).

Analogously can be obtained:

1-benzoyl-1-cyano-3-diethylaminopropane citrate, m.p. = 89°C (from alcohol ether).

EXAMPLE 10

1-p-Fluorobenzoyl-1-N-dimethyl-carbamoyloxy-3-N-(N'-phenyl)piperazino-propane dihydrochloride.

To 17.6 cc of a 20% solution of phosgene in toluene cooled to 0°C and stirred, during half an hour is added a solution of 10 g. of 1-p-fluorobenzoyl-1-hydroxy-3-N-(N'-phenyl)piperazino-propane and 3.84 g. of triethylamine in 130 cc. anhydrous chloroform. Once the addition is completed, the product is stirred at room temperature for 5 hours, it is then cooled to 0°C and 18 cc. of a benzene solution of 3.96 g. of dimethylamine are added. The cooling bath is removed and stirring is continued for 2 hours. The solution is washed several times with water, dried over $Na_2SO_4$ and evaporated to dryness.

The residual oil is transformed into the corresponding dihydrochloride: m.p. 208°C (from alcohol).

Analogously can be obtained:

1-p-Fluorobenzoyl-1-N-tert. butyl-carbamoyloxy-3-N-(N'-phenyl)piperazino-propane, m.p. 130°C (from alcohol).

We claim:

1. A 1,3-disubstituted-3-aroyl propane having the formula:

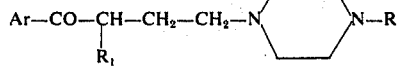

wherein:

Ar is phenyl, halo-phenyl or methoxy substituted phenyl;

$R_1$ is hydroxy, acetyloxy, phenoxy, mono-alkylcarbamoyloxy having up to 5 carbon atoms or dialkylcarbamoyloxy having up to 4 carbon atoms in each alkyl group thereof;

and

R is phenyl, o-methoxyphenyl or 2-pyridyl; or the pharmaceutically acceptable salts thereof.

2. 1-p-fluorobenzoyl-1-hydroxy-3-(N'-phenyl)-piperazino-propane as defined in claim 1 or the pharmaceutically acceptable salts thereof.

3. 1-p-fluorobenzoyl-1-acetyloxy-3-(N'-phenyl)-piperazino-propane as defined in claim 1 or the pharmaceutically acceptable salts thereof.

4. 1-p-fluorobenzoyl-1-phenoxy-3-(N'-phenyl)-piperazino-propane as defined in claim 1 or the pharmaceutically acceptable salts thereof.

5. 1-benzoyl-1-hydroxy-3-(N'-phenyl)piperazino-propane as defined in claim 1 or the pharmaceutically acceptable salts thereof.

6. 1-p-chlorobenzoyl-1-hydroxy-3-(N'-phenyl)-piperazino-propane as defined in claim 1 or the pharmaceutically acceptable salts thereof.

7. 1-p-methoxybenzoyl-1-hydroxy-3-(N'-phenyl)-piperazino-propane as defined in claim 1 or the pharmaceutically acceptable salts thereof.

8. 1-p-fluorobenzoyl-1-hydroxy-3-(N'-o-methoxyphenyl)-piperazino-propane as defined in claim 1 or the pharmaceutically acceptable salts thereof.

9. 1-p-fluorobenzoyl-1-hydroxy-3-(N'-2-pyridyl)-piperazino-propane as defined in claim 1 or the pharmaceutically acceptable salts thereof.

10. 1-p-fluorobenzoyl-1-N-dimethyl-carbamoyloxy-3-(N'-phenyl)-piperazino-propane as defined in claim 1 or the pharmaceutically acceptable salts thereof.

11. 1-p-fluorobenzoyl-1-N-tert-butyl-carbamoyloxy-3-(N'-phenyl)-piperazino-propane as defined in claim 1 or the pharmaceutically acceptable salts thereof.

* * * * *